United States Patent
Wong et al.

(10) Patent No.: US 9,554,778 B2
(45) Date of Patent: Jan. 31, 2017

(54) RESPONSIVE POWER SAVING IN ULTRASOUND

(71) Applicants: King Yuen Wong, Issaquah, WA (US); Chi Hyung Seo, Sammamish, WA (US)

(72) Inventors: King Yuen Wong, Issaquah, WA (US); Chi Hyung Seo, Sammamish, WA (US)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 401 days.

(21) Appl. No.: 14/076,067

(22) Filed: Nov. 8, 2013

(65) Prior Publication Data

US 2015/0133786 A1    May 14, 2015

(51) Int. Cl.
*A61B 8/00* (2006.01)

(52) U.S. Cl.
CPC .............. *A61B 8/56* (2013.01); *A61B 8/4427* (2013.01); *A61B 8/54* (2013.01); *A61B 8/463* (2013.01)

(58) Field of Classification Search
CPC ..................................... A61B 8/54; A61B 8/56
See application file for complete search history.

(56) References Cited

U.S. PATENT DOCUMENTS

| 6,123,670 | A  * | 9/2000  | Mo ........................ A61B 8/469 600/447 |
| 6,610,011 | B2   | 8/2003  | Emery |
| 7,338,446 | B2   | 3/2008  | MacDonald et al. |
| 7,984,651 | B2   | 7/2011  | Randall et al. |
| 2008/0112265 | A1 | 5/2008  | Urbano et al. |
| 2009/0124903 | A1* | 5/2009 | Osaka ...................... A61B 8/12 600/443 |
| 2012/0323121 | A1 | 12/2012 | Miller |

* cited by examiner

*Primary Examiner* — Joseph M Santos Rodriguez

(57) ABSTRACT

Responsive power saving is provided for ultrasound imaging, such as in portable ultrasound systems. By reducing scan line density in response to removal of a transducer from a patient, power usage may be reduced while still monitoring for return of the transducer to the patient. By disabling the display, power usage may be reduced while still monitoring for return of the transducer to the patient. All or most electronics not associated with monitoring for the return of the transducer to the patient may be disabled or not used to conserve power.

12 Claims, 2 Drawing Sheets

RESPONSIVE POWER SAVING IN ULTRASOUND

BACKGROUND

The present embodiments relate to ultrasound imaging. In particular, power savings are provided for ultrasound systems.

Ultrasound systems use power to acoustically scan and process the resulting data. For environmental reasons, reducing power is beneficial. Reducing power is more imperative in a portable and/or battery powered ultrasound system.

Ultrasound systems may use a timeout to save power. Once the ultrasound system has ceased interacting with the system, a timer begins. Upon expiration of a time limit, the ultrasound system is placed into a screen saver mode, ceases transmitting, and/or enters a standby (e.g., sleep) mode where scanning ceases. The user must revive the ultrasound system from the standby mode to resume scanning again. The revival may take a frustrating amount of time. The ceasing transmitting or screen saver mode where the time limit is short may cause interruption when undesired.

Proposals have been made to reduce power while still providing for scanning. For example, a transmit voltage is reduced due to detection of user inactivity. As another example, various scanning parameters and use of electronics are changed to reduce power while still producing diagnostic images. However, these changes assume power consumption distribution in a manner that may not be accurate.

BRIEF SUMMARY

By way of introduction, the preferred embodiments described below include systems, methods, computer readable media, and instructions for responsive power saving in ultrasound, such as in portable ultrasound systems. By reducing scan line density in response to removal of a transducer from a patient, power usage may be reduced while still monitoring for return of the transducer to the patient. By disabling the display, power usage may be reduced while still monitoring for return of the transducer to the patient. All or most electronics not associated with monitoring for the return of the transducer to the patient may be disabled or not used to conserve power.

In a first aspect, a method is provided for responsive power saving in portable ultrasound. A transducer of a portable ultrasound system first scans a patient with a first line density. An image of the patient is displayed. The image is responsive to the first scanning. The transducer of the portable ultrasound system continues to scan with the first line density. A position of the transducer away from the patient is detected in response to the continued scanning. The transducer of the portable ultrasound system scans with a second line density less than the first line density. This scanning is in response to the detecting the position of the transducer away from the patient. A display of the portable ultrasound system is disabled in response to the detecting of the position of the transducer away from the patient.

In a second aspect, a system is provided for responsive power saving in ultrasound. A transmit beamformer connects with a transducer. The transmit beamformer is configured to transmit beams of acoustic energy. A receive beamformer connects with the transducer. The receive beamformer is configured to generate receive beams in response to the transmit beams of acoustic energy. A B-mode detector is configured to detect intensity of the receive beams. A processor connects with the B-mode detector, the transmit beamformer, and the receive beamformer. The processor is configured to control the transmit and receive beamformers to scan a patient at a first resolution and first frame rate and, when the transducer directed to air, to monitor for placement of the transducer against the patient at a second resolution lower than the first resolution and a second frame rate greater than the first frame rate. The monitoring is a function of an output of the B-mode detector.

In a third aspect, a non-transitory computer-readable medium has stored therein instructions executable by a processor for responsive power saving in ultrasound. The instructions include detecting displacement of a transducer of an ultrasound system from a patient, reducing power usage by the ultrasound system in response to the detecting of the displacement of the transducer from the patient, performing only scanning and calculations for detecting user resumption of scanning the patient while operating with the power usage of the reducing, and activating other calculations in response to the detecting of user resumption.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Processing power is adjusted in a portable ultrasound system. Power is consumed by computing resources used to produce high quality images. These resources are unnecessary when the user is not actively scanning the patient. By reducing use of these resources with or without changing scanning, power savings may be substantial. For example, modem ultrasound machines may resort to graphics processing units and/or high-powered computer processing units to render high quality images. By turning off these components, power may be saved.

To provide a fast response to the user re-engaging in scanning, scanning continues but in the reduced power state while the transducer is spaced from the patient. The continued scanning allows for rapid resumption of scanning in order to provide a satisfactory user experience. If the probe is scanning in the tissue, the system goes back to normal scanning mode rapidly due to the detection from the scanning.

Portable ultrasound systems may particularly benefit from this approach. One of the benefits of portable ultrasound systems is having a freedom of movement. However, freedom of movement also implies relying on battery power. One method to reduce power consumption is to detect if the probe is actively scanning in the air or tissue. Power consumption is reduced once scanning of air is detected, switching from a diagnostic imaging state to a pseudo freeze state. In the pseudo freeze state, the number of scanning lines is reduced, allowing an increase in frame rate. Unnecessary signal processing and display are reduced to conserve power. Acquisition activities are limited to just enough to detect the user re-engaging scanning and thus be able to resume the normal scanning.

Figure 1:
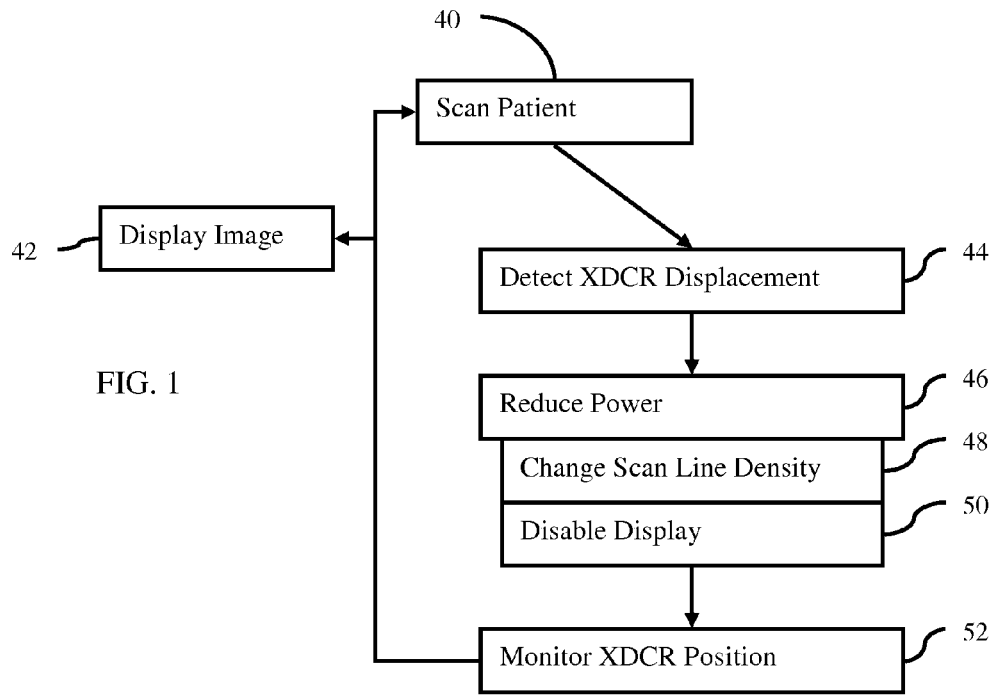
FIG. 1 is a flowchart of one embodiment of a method for responsive power saving in ultrasound.

FIG. 1 is a flowchart of one embodiment of a method of responsive power saving in ultrasound. Power is saved while still providing response to the user reengaging the transducer for scanning the patient. Rather than entering a freeze or standby state, a pseudo freeze state allows for continued reduced power scanning to detect whether the transducer is repositioned against the patient. The scan line density, use of the display, and/or other calculations and electronics in the ultrasound system are limited, shut down, turned off, or otherwise disabled to conserve power.

Figure 4:
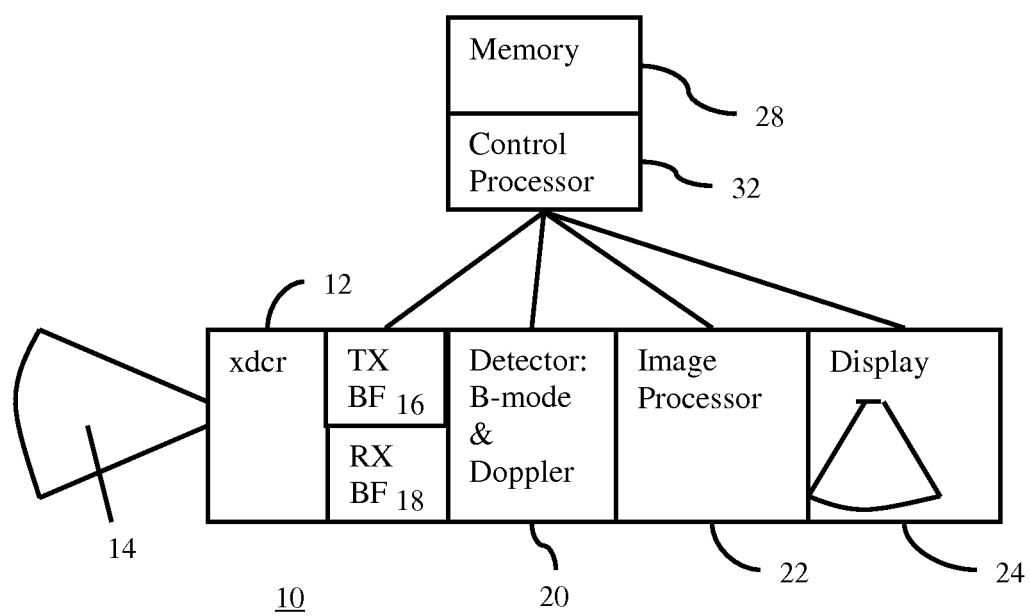
FIG. 4 is a block diagram of one embodiment of a medical diagnostic ultrasound imaging system for responsive power saving.

The method is implemented with the system 10 of FIG. 4, or other ultrasound imaging system. For example, the method is performed with a handheld ultrasound system weighing less than six (e.g., about two) pounds. The acts are performed by or with the handheld ultrasound system. In other embodiments, other ultrasound systems, such as cart mounted systems with power drawn from a plug, perform the acts.

The method is performed in the order shown or another order. Additional, different, or fewer acts may be performed. For example, act 48 is not performed while act 50 is performed, or vice versa. As another example, acts 48 and 50 are not performed but other power reductions are used.

In act 40, a patient is scanned. An ultrasound system, such as a portable ultrasound system, uses a transducer to scan the patient. Electrical waveforms are converted into acoustic energy by elements of the transducer. The responsive echoes are received and converted into electrical signals by the elements. By steering the transmissions and receptions, a region of the patient is scanned.

Any scan sequence may be used. For example, linear, sector, Vector®, or other scan formats are used. Transmit and receive beams are formed along a plurality of scan lines distributed through the region of the patient. Any density of scan lines, depth of field of view, and lateral extent of the field of view may be used. In one embodiment, tens or hundreds of scan lines are used for a single scan of the patient. Responsive data is organized as a frame of data representing the patient along the scan lines at a give time corresponding to the period to scan along all of the scan lines. Any scan line density (i.e., number of scan lines per lateral spacing or within a given field of view) may be used.

Other characteristics of the scanning may be predetermined or user selected. For example, the field of view (depth and lateral extent), transmit power for each transmit beam, transmit aperture, and receive aperture are programmable and are set for a given scanning session. The scanning is for one, two, or three-dimensional scanning.

The scanning is performed for a given mode of imaging. B-mode imaging scans along each scan line once. Doppler (e.g., flow or color mode) imaging uses a sequence of pulses in a pulse repetition interval along each scan line. Other modes include M-mode or spectral Doppler. In a duplex mode, scans for different types of imaging are interleaved, such as combining B-mode and Doppler mode scans. Triplex modes using three types of scanning may be provided. Alternatively, the scanning is for a single mode.

In act 42, an image of the patient is displayed. The received data from the scanning is beamformed. The beamformed data is detected, such as using B-mode or other intensity detection, Doppler estimation (e.g., velocity, energy, and/or variance), M-mode, spectral Doppler, contrast agent, or other detection. Filtering and/or compounding may be applied to the frames of data. Temporal and/or spatial filtering may be performed. Frequency filtering, such as to isolate the information at a harmonic of the transmit frequency, may be used. Compounding may interpolate additional information, stitch together data from multiple focal ranges, provide for steered spatial compounding, provide for frequency compounding or may isolate information (e.g., compounding for cubic fundamental imaging). Gain compensation, tissue equalization, spatial transformations, contrast enhancement, noise reduction, border enhancement, speckle suppression, scan conversion, and/or display mapping may be applied. Any now known or later developed data or image processing in ultrasound may be used.

The data received from the scanning of act 40 is used to generate an image. The image is responsive to the scanning of the patient. The image represents an internal region of the patient. The skin may be represented as well. The image is a B-mode, Doppler, M-mode, spectral Doppler, contrast agent, other imaging mode, or combinations thereof (e.g., duplex or triplex imaging mode). A single image or a group of images is displayed. Alternatively or additionally, an ongoing sequence of images is displayed.

The scanning of the patient in act 40 continues for acquiring additional frames of data. Similarly, the display in act 42 of an image continues for each frame or group of acquired frames.

Figure 2:
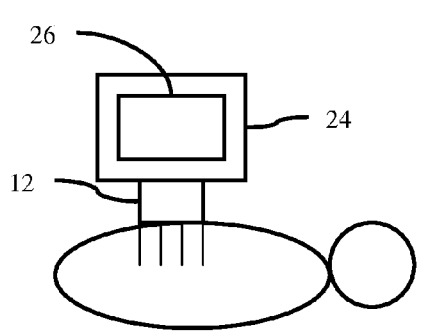
FIG. 2 illustrates one embodiment of a handheld ultrasound system with a transducer against a patient.

FIG. 2 shows the transducer 12 of the ultrasound system held against the patient. The user, the patient, or a mechanical device holds the transducer 2 against the patient for on-going, real-time, or intermittent scanning. The display 24 shows one or more images 26 resulting from the scanning. In FIG. 2, the ultrasound system is a handheld or portable system operating on battery power with the display 24 connected with the transducer 12. In other embodiments, the display 24 of the portable system is in a separate housing. In yet other embodiments, the display is on a cart and the transducer 12 is a transducer probe connected by coaxial cables to the cart-mounted ultrasound system.

Figure 3:
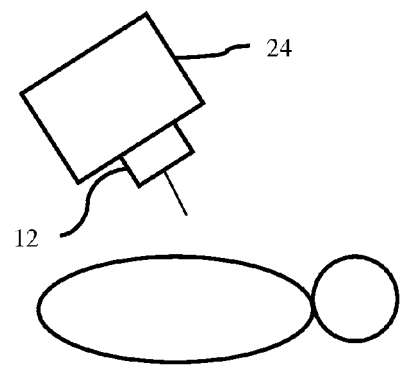
FIG. 3 illustrates the handheld ultrasound system of FIG. 2 with the transducer continuing to scan, but with fewer scan lines, when spaced from the patient.

In act 44 of FIG. 1, positioning of the transducer 12 away from the patient is detected. FIG. 3 shows the transducer 12 being displaced away from the patient. The displacement may be by millimeters, such as sufficient to remove the acoustic coupling of the face or window of the transducer 12 from the skin of and/or acoustic coupling gel on the patient. The displacement may be greater, such as further than a depth of scanning (e.g., 10 centimeters or more).

One or more frames of data or other data acquired by the scanning in act 40 used for displaying images are also used to detect the displacement. Alternatively, separate scans for detecting displacement are interleaved with the scanning for the display of images. Whether using the imaging data or interleaved scan data, the position of the transducer away from the patient is detected in response to the scanning of act 40. In yet other alternative embodiments, a motion sensor, transducer position sensor, optical video, or other sensor is used to detect the displacement.

Decoupling of the transducer 12 from the patient is detected. Any detection technique may be used. In one embodiment, air adjacent to the transducer is detected from the scan data. Air may lack speckle, so a speckle threshold is applied to detect the air. In other embodiments, air is detected by a consistent lack of echo signals. Low backscatter may indicate air. A same signal for a sufficiently long time (e.g., 10 seconds) may indicate air. In other embodiments, motion of the probe is detected regardless of detecting any air. If the probe rotates away and/or moves away from the patient as shown by anatomy or speckle tracking, displacement away from the patient is detected.

The ultrasound system continuously (e.g., real-time), periodically, or occasionally analyzes the acquired data to determine whether the transducer 12 is touching the patient. If the transducer transitions away from the patient, such as shown in FIG. 3, this transition is detected. The sonographer may be involved in conversation, may be examining other sensors or information in a patient room, or may otherwise be distracted or change focus away from scanning. Similarly, the sonographer may be, at least temporarily, done scanning and imaging the patient.

Rather than continue to scan for imaging, the power usage may be reduced in act 46 in response to detecting the displacement of the transducer from the patient. The amount of power drawn from a power supply, such as battery, is reduced while the transducer is not in contact with the patient. As soon as the transducer losing contact with the patient is detected, the system automatically switches to a pseudo freeze state that conserves power.

The power is conserved by reducing the quality of the acquired data, limiting features or processing, ceasing display, and/or limiting other operations that use power by the ultrasound system. Scanning is continued despite the loss of contact to detect when the transducer is repositioned against the patient. The sonographer may return to scanning the patient and delay by the ultrasound system in reinitiating the imaging is undesired. For more rapid return to imaging, the scanning continues in the pseudo freeze state, but with reduced power consumption.

Any power reduction may be used. Acts 48 and 50 show two possible sources of power reduction. Only one, none, or both acts are performed. Other power reduction acts may additionally or alternatively be used.

In act 48, the scan line density is changed. The scanning for two or three-dimensional imaging uses a number of scan lines in the region. For one-dimensional scanning, multiple lines may be scanned for providing different information. Once the transducer 12 is not against the patient, the number of scan lines is reduced. The number of scan lines per area or volume is reduced. Any reduction may be used, such as by a factor of ten or more. For example, thirty two, sixty four, one hundred twenty eight, or other number of scan lines are used for imaging. For power conservation, as few are one scan line is used. One, two, four, eight, sixteen or other number of scan lines may be used once the transducer 12 is spaced from the patient.

The scanning continues, but with the reduced scan line density. The reduction in scan line density is alternatively or additionally due to a reduction in the number of modes of detection being used. For example, Doppler and B-mode scanning may use different scan lines. By ceasing Doppler or B-mode imaging, the number of scan lines being used is reduced. By only using one mode (e.g., B-mode) of scanning, the power may be reduced by a reduction in scan line density and/or use of less electronics.

The reduction may be the number of scan lines used for a given mode. For example, B-mode scanning continues, but with fewer scan lines. The transducer of the ultrasound system transmits fewer beams per frame or per unit of time as a result of the reduction in scan line density.

Other scanning related reductions in power may be used in addition or as an alternative to scan line density change. The scanning may be performed with a lesser transmit power (e.g., less amplitude), smaller transmit aperture, smaller receive aperture, and/or smaller field of view (e.g., less lateral and/or depth extent) than for scanning for imaging. These changes in scanning may reduce the power of the generated acoustic energy and/or the power consumed by the electronics used to generate the acoustic energy. For example, the transmit amplitude, transmit aperture, and receive aperture are each reduced by half. This results in acoustic signals with less energy as well as less electronics to generate the acoustic signals, both resulting in less power consumption.

The reduction in power usage allows continued scanning while extending battery life and/or optimizing power usage. Since the sonographer may return to scanning the patient, the reaction to the return is as rapid as possible. The frame rate of the scanning may be increased to more rapid detection of the return to the patient while still reducing power. Part of the offset in power and the lesser scan depth and/or the fewer number of scan lines may be used for scanning with a greater frame rate. The frame rate for monitoring in act 52 is greater than the frame rate for scanning and imaging in acts 40 and 42. A fast response to the user re-engaging in scanning may provide a more desirable user experience rather than having to power on the ultrasound system. In alternative embodiments, the scan or frame rate of the monitoring in act 52 is less than or the same as the scan or frame rate of act 40.

For further power reduction, other processing and associated electronics and calculations may be disabled. For example, filtering, compounding or other operations are not performed. Electronics dedicated to these specific operations are not clocked, not used, shut down, instructed not to operate, or otherwise disabled from operating. Any technique for disabling the electronics so that they do not perform calculations or processing for a particular operation may be used. As a result, less power is consumed. Parts of the electronics may be disabled. For example, some channels of the transmit and receive beamformers are disabled by not being used.

Electronics that perform different operations for distinct purposes, such as a control processor, may perform fewer calculations or less processing. For example, data transfers are not needed for programming disabled beamformer channels or other disabled electronics, resulting in fewer calculations and associated power consumption.

In one embodiment, all but one detector are disabled. For example, only the B-mode detector remains active while a Doppler detector is disabled. Other processes may be ceased to conserve power. By turning off advanced and basic features other than those needed for user interface and the monitoring of act 52, power consumption may be optimized. Real-time or periodic analysis of user input and/or scan data for detecting resumption of scanning the patient is provided without any other or with limited other processing.

In act 50, the display of the ultrasound system is disabled. The display is disabled by freezing the image (e.g., disabling updates), turning off a back light, deactivating, not clocking, not changing, turning off, powering down, or otherwise not using the display. FIG. 3 shows the display 24 without an image as an example. By turning off and/or freezing the image on the display 24 in response to detecting that the transducer 12 is positioned away from the patient, power may be conserved. Power usage is reduced.

By performing the monitoring of act 52 and power reduction of act 46 in an ongoing manner, the battery life may be extended. The amount of power used, whether from a battery or not, may be optimized. Since the scanning for diagnostic or therapeutic purposes may only be temporarily halted, some scanning continues in the monitoring of act 52 to monitor for repositioning the transducer 12 against the patient to resume imaging.

The monitoring of act 52 performs the same detection as used in act 44. When the data indicates no air or signals associated with coupling to tissue, displacement back to the patient is detected. By repeating the detection, a change in coupling between the transducer 12 and the patient may be detected. In alternative embodiments, different detection is used to monitor for coupling than is used for detecting decoupling. For example, signal amplitude or transducer motion with tissue tracking is used to detect decoupling. The monitoring for return to coupling is performed with speckle analysis. If speckle is detected for a location, sub-region, or substantial amount (e.g., 60%) of the field of view, coupling is identified as having occurred.

During the monitoring of act 52, the reduction in power usage of act 46 continues. Only operations associated with monitoring in act 52 using scanning and user interface monitoring are performed with other operations, calculations, and/or electronics disabled or operating in a reduced power state. Only scanning and calculations for detecting user resumption of scanning the patient are performed, providing on-going reduction in power usage.

Once the monitoring indicates transducer 12 contact with the patient or other coupling, the scanning of act 40 and imaging of act 42 are performed. The scanning of act 40 for imaging of act 42 and the display in act 42 are repeated. In other embodiments, the transducer 12 begins operation in the reduced power state until coupling is detected. Acts 40 and 42 are then performed initially after the monitoring of act 52.

The ultrasound system automatically switches back to a normal or previously configured operating state. The line density, electronics, advanced processing, basic processing, or other disabled features resume operation. Other calculations are activated in response to detecting sonographer resumption of diagnostic or therapeutic use of the ultrasound system. In alternative embodiments, the return to the previous operation state is gradual, such as first increasing line density, transmit amplitude, and apertures for B-mode scanning, then adding operation for other imaging modes, and then adding filtering, compounding or other advanced features over several seconds.

FIG. 4 shows one embodiment of a medical diagnostic ultrasound imaging system 10 with responsive power saving. Any known or future dedicated ultrasound imaging system may be used. In other embodiments, the ultrasound imaging system 10 may be a computer, a workstation, a server, and/or an image database system for medical diagnosis with ultrasound images.

The system 10 implements the method of FIG. 1 or a different method. The system 10 optimizes consumption of power where the transducer 12 is purposefully or inadvertently removed from the patient but may return for further examination. The power consumption is optimized using detection of coupling of the transducer 12 with the patient.

In one embodiment, the imaging system 10 is a cart-based imaging system. In another embodiment, the imaging system 10 is a portable system, such as a briefcase-sized system or laptop computer-based system. Other embodiments include handheld ultrasound systems. For example, one or more housings are provided where the entire system 10 is small and light enough to be carried in one or both hands and/or worn by a user. The processors 22, 32, transducer 12, display 24, and/or other components are provided in a single housing. In another example, the transducer 12 is in one housing to be held by a person, and the imaging components and display 24 are in another housing to be held or worn by the person. Coaxial cables connect the two housings. As another example, the transducer 12 and imaging components are in one housing, and the display 24 is in another housing. In yet another example, the transducer 12 is in one housing connected by a cable 20 to a housing for the imaging components, including the image processor 22 and user input, and the display 24 is in a third housing hinged or rotatably connected with the housing of the image processor 22.

In one embodiment, the transducer 12 with or without the beamformers 16, 18, detectors 20, image processor 22, control processor 32, memory 28, and/or other components, wirelessly communicates with the display 24 and/or other components. For example, the display 24, control processor 22, image processor 22, and detectors 20 are part of a main unit or control station that wirelessly receives beamformed or non-beamformed data from a handheld and battery operated transducer probe. Based on detection of scanning air, the battery operated transducer probe may be reconfigured to enter the pseudo freeze or reduced power state. The main unit may or may not also be reconfigured to enter the pseudo freeze or reduced power state.

In any embodiment, the entire handheld system may weigh less than about 6 pounds, but may weigh more. For example, the handheld system weighs less than about 2 pounds (e.g., 1.6 pounds), a weight similar to commonly used, portable medical equipment and more naturally born by medical professionals without burden. "About" allows for manufacturing tolerances. The size of the handheld device may allow placement in a shirt or lab coat pocket.

The weight and size may be achieved by integrating the imaging functions into a limited number of chips or small scale circuits, such as processors, field programmable gate arrays, and/or application specific integrated circuits. For example, one or a few analog application specific integrated circuits are provided adjacent the transducer for transmit operation and channel reduction on receive. One or a few analog-to-digital converter chips connect with one or a few field programmable gate arrays implementing receive beamforming, filtering, detection, scan conversion, and other operations. A battery powers the system.

The system 10 includes the transducer 12, a transmit beamformer 16, a receive beamformer 18, one or more detectors 20, an image processor 22, a display 24, a control processor 32, and a memory 28. Additional, different, or fewer components may be used. For example, a cable connecting the transducer 12 to the receive beamformer 18 is provided, and/or a cable connects the display 24 to the image processor 22. While shown as separate, different components may be integrated together on a same device or devices.

The transducer 12 is an array of elements. Any array may be used, such as a linear, phased, curved linear, or other now known or later developed array. Any number of elements may be used, such as 64, 96, 128, or other numbers. One, two, or other multi-dimensional (e.g., 1.25D, 1.5D, or 1.75D) arrays may be provided.

The elements are piezoelectric or capacitive membrane elements. A single layer of transducer material is provided for each element. Alternatively, the elements are multi-layered, such as having at least two layers of piezoelectric ceramic transducer material. The transducer material may be a semiconductor substrate with one or more flexible membranes (e.g., tens or hundreds for each element) formed within or on the semiconductor substrate. The transducer elements may also include any number of different layers, such as matching layers, flex circuit layers, signal traces, electrodes, a lens and/or a backing block.

The transducer 12, for example, is in an ultrasound probe connected with an ultrasound system or is in a housing for the entire system 10. The transducer 12 connects with the transmit beamformer 16 and the receive beamformer 18.

The transmit beamformer 16 connects with electrodes on one side of the elements, and the receive channels connect with electrodes on an opposite side of the elements. Passive or active switching grounds the electrodes not being used, such as grounding transmit side electrodes during receive operation. Alternatively, the transmit and receive beamformers 16, 18 connect to the same electrodes of the elements of the transducer 12 through a transmit/receive switch.

The transmit beamformer 16 is a plurality of transistors, such as high power transistors for generating relatively delayed unipolar or bipolar waveforms in channels for some or all of the elements. Amplifiers, delays, phase rotators, waveform generators, memories, or other components may be provided for the channels to focus and/or apodize.

In response to signals from the transmit beamformer 16, the transducer 12 generates acoustic transmit beams. The acoustic beams are focused to different locations to scan a two or three-dimensional region 14. The scan format is linear, sector, Vector®, or other now known or later developed scan format. The scan format includes a set or programmable number of beams within the region 14, such as 50-150 beams. The depth of the region 14 may be set or programmable.

The transducer 12 is operable to receive acoustic signals and convert the acoustic signals into electrical energy. For example, the transducer 12 is operable to acquire ultrasound signals by receiving echo signals at one or more elements. The ultrasound signals include information for C-mode (e.g., Doppler mode, flow mode, velocity, energy, or variance), B-mode (grey-scale), and other tissue or flow information.

The receive beamformer 18 is a digital or analog beamformer. The receive beamformer 18 is an application specific integrated circuit, processor, field programmable gate array, digital components, integrated components, discrete devices, or combinations thereof. The receive beamformer 18 includes, but is not limited to, amplifiers, delay memories, a delay calculator, a phase rotator, a demodulator, a baseband filter, and/or channel adders for different channels to form beams. A summer common to multiple channels may be used.

The receive beamformer 18 receives analog or digital information for the elements or groups of elements. The receive beamformer 18 apodizes and relatively focuses the received samples, creating receive beams responsive to the transmit beams. Electrical signals received from the transducer elements are relatively delayed and summed. Amplifiers may be provided for apodization. In one embodiment, the delays are implemented as memories for storing channel data (e.g., samples from each element). One or more memories may be used. For example, two memories or sets of memories operate in a ping-pong fashion to store data from elements and read data out for beamforming. Each memory or set stores element data for an entire scan. As one memory or set is storing, the other memory is outputting. By reading data out of the memory from selected memory locations, data associated with different amounts of delay is provided. The same data may be used for sequentially or parallel forming receive beams along different scan lines. Other memories may be used, such as a plurality of first-in, first-out buffers for delaying based on length and/or timing of input into the buffers. In other embodiment, the delays are implemented as buffers.

Other components may be provided separate from or implemented on a same device as the receive beamformer 18. For example, filters are provided for spatial and/or temporal filtering beamformed data. As another example, decimators are provided. In other examples, filters for filtering coherent data (prior to detection) are provided. As yet another example, buffers for synthetic beam combinations, harmonic imaging, or other compounding are provided.

The detector 20 is one or more different types of detectors. For example, both B-mode and Doppler (color-mode) detectors are provided. Other types of detectors include contrast agent detectors. Using the B-mode or Doppler detector with buffers, phase rotators, and/or summers, information associated with contrast agent return and not tissue or fluid return may be detected, such as using the cubic fundamental response.

The B-mode detector determines an intensity of the echo signals in the receive beams. The envelope or other characteristic of the receive beamformed data responsive to tissue, fluid or other reflector is detected. The detection is performed for an entire scan or a frame of data for one image.

The Doppler detector is an estimator that estimates velocity, power, variance or combinations thereof for a region of interest. A clutter filter may be provided to isolate information for slowly moving tissue or more rapidly moving fluid. The estimation is performed for a region on data separate from or in addition to the data used for B-mode detection.

The image processor 22 may include a persistence filter, spatial filters, log compressor, scan converter, compound processors, or combinations thereof. For example, detected data is persisted and log compressed. The log-compressed data is scan converted. The scan conversion converts the r-θ or polar coordinate data into a Cartesian coordinate format for the display 24. While shown between the display 24 and the detectors 20, the image processor 22 may be distributed through the data chain for performing any operations to generate the image for the display 24. The image processor 22 is one or more application specific integrated circuits, general processor, graphics processing unit, digital signal processor, field programmable gate array, analog circuit, digital circuit, discrete components, or combinations thereof.

The control processor 32 connects with the detector 20, the transmit beamformer 16, the receive beamformer 18 and the display 24. In other embodiments, the control processor 32 does not connect with the display 24, but instead controls the display by generation or not of images.

The control processor 32 is implemented by a general processor, control processor, digital signal processor, application specific integrated circuit, field programmable gate array, digital circuit, memory, combinations thereof, or other now known or later developed processor. In one embodiment, the control processor 32 is a single device. In other embodiments, the control processor 32 includes a plurality of devices, such as distributed processors. The control processor 32 is separate from the image processor 22, but may be part of the image processor 22 or share processing resources in other embodiments.

The control processor 32 controls operation of various components of the ultrasound system. For example, the control processor 32 controls operation of the transmit and receive beamformers 16, 18 to scan the patient at a given resolution, line density, scan pattern, frame rate, transmit amplitude, transmit aperture, and receive aperture. As another example, the control processor 32 controls operation of the detectors 20, such as whether a particular type of detection is performed and operating characteristics of the detection (e.g., cutoff filter frequency or type of flow estimation). Similarly, the control processor 32 controls the image processor 22, such as whether to perform processes (e.g., filtering and/or compounding) and the characteristics of the processes being performed. The control processor 32 controls the display 24, such as controlling updating of images, back lighting, clocking, or other display operation. The control processor 32 may control delivery of power to one or more components, turn the components on or off, or otherwise control power consumption by the components.

The control processor 32 is configured by hardware and/or software to detect the position of the transducer 12 relative to the patient. By receiving data from the receive beamformer 18, detector 20, image processor 22, or display 24, the control processor 32 detects whether the transducer is coupled to the patient. Alternatively, the control processor 32 causes one of these other components to detect and receives results of the detection. The control processor 32 monitors for a change in coupling. When the transducer 12 is directed to or scanning air, the control processor 32 monitors for placement of the transducer against the patient. During this monitoring, the power use of other components is reduced. For example, the beamformers 16, 18 are caused to scan at a resolution lower than used for imaging the patient. The frame rate may be increased for the monitoring of reestablishing contact as compared to the frame rate used for imaging.

In one embodiment, the control processor 32 causes only the B-mode detector 20, part of the transmit beamformer (e.g., ⅛ of the channels), and part of the receive beamformer (e.g., ¼ of the channels) to operate while the image processor 22, Doppler detector 20, display 24, remaining parts of the beamformers 16, 18, spatial filter, temporal filter, compound processor, and other electronics of the system 10 are disabled. Further power reduction may be provided by controlling the beamformers 16, 18 to use a smaller field of view, fewer scan lines, and smaller transmit amplitude in addition to the limited apertures and corresponding fewer channels of the beamformers 16, 18 than used for the imaging.

The reduction in power or operation is performed in response to detecting decoupling of the transducer 12 from the patient. For example, image data, Doppler data, or B-mode data with or without compounding and/or filtering is examined to detect whether any portion or the near field portion of the scan region 14 is passing through air. If the transducer 12 is directed to air, the pseudo freeze state is activated to reduce power.

After reducing power, the control processor 32 uses output from the B-mode detector to monitor for coupling. As long as coupling is not detected, the lower power operation continues. Once complete or partial coupling of the transducer 12 to the patient is detected, normal scanning and imaging resumes. In response to acoustic coupling of the face of the transducer to the patient without intervening air being detected, the disabled electronics or some of the disabled electronics, depending on the configuration for imaging, is reactivated and/or used for imaging or therapy by the control processor 32.

The display 24 is a liquid crystal display, monitor, plasma screen, projector, printer, combinations thereof, or other now known or later developed display device. In one embodiment, the display 24 is a small, digital LCD, such as associated with handheld devices (e.g., cellular phones or personal data assistants). For example, the display 24 is less than 10 inches along a longest dimension, such as being about 3×4 inches. Any number of pixels may be provided. In alternative embodiments, the display 24 is larger, such as associated with personal computers, laptop computers, or television displays.

The display 24 operates to generate an image from data provided by the image processor 22. The display 24 receives scan converted ultrasound data and displays an image. An image is generated for each frame of data. For real-time ultrasound imaging, the display 24 receives frames of data and displays a sequence of ultrasound images each representing the region 14 or overlapping portions thereof. Images responsive to the scans of the patient are displayed on the display 24 during normal scanning.

For reduced power operation, the display 24 is disabled, such as by not updating, turning off, powering down, or otherwise ceasing operation of the display 24. In alternative embodiments, a low power usage indicator of low power operation (e.g., a blinking dot or simple text) is displayed without displaying any image of the patient. In yet other alternative embodiments, a low resolution image of the patient, air, or both generated from the monitoring scan during decoupling is displayed.

The memory 28 is a logic encoded medium having stored therein data representing executable instructions for automatic gain control. For example, software is stored and executable by a processor. The instructions for implementing the processes, methods and/or techniques discussed herein are provided on computer-readable storage media or memories, such as a cache, buffer, RAM, removable media, hard drive or other computer readable storage media. Logic encoded storage media include various types of volatile and nonvolatile storage media. The functions, acts or tasks illustrated in the figures or described herein are executed in response to one or more sets of instructions stored in or on logic encoded storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. In another embodiment, the memory 28 is within a handheld ultrasound system with one or more housings.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for responsive power saving in portable ultrasound, the method comprising:
   first scanning, with a transducer of a portable ultrasound system, a patient with a first line density;
   displaying an image of the patient, the image responsive to the first scanning;
   second scanning, with the transducer of the portable ultrasound system, with the first line density;
   detecting a position of the transducer away from the patient in response to the second scanning;
   third scanning, with the transducer of the portable ultrasound system, with a second line density less than the first line density, the third scanning being in response to the detecting the position of the transducer away from the patient; and
   disabling a display of the portable ultrasound system in response to the detecting of the position of the transducer away from the patient.

2. The method of claim 1 wherein the first and second scanning comprise duplex mode scanning, and wherein the third scanning comprises only B-mode scanning.

3. The method of claim 1 wherein the third scanning comprises scanning with the second line density being less by a factor of ten or more.

4. The method of claim 1 wherein detecting the position of the transducer away from the patient comprises detecting air adjacent to the transducer from data acquired with the second scanning.

5. The method of claim 1 wherein detecting the position of the transducer away from the patient comprises detecting a decoupling of the transducer from the patient.

6. The method of claim 1 wherein disabling comprises freezing the image.

7. The method of claim 1 wherein disabling comprises turning off the display.

8. The method of claim 1 wherein third scanning comprises scanning with a greater frame rate than the first and second scanning.

9. The method of claim 1 further comprising:
   monitoring for a position of the transducer against the patient with the third scanning; and
   repeating the first scanning and displaying in response to detection of the position of the transducer against the patient with the monitoring.

10. The method of claim 9 further comprising:
    only performing the monitoring and third scanning with electronics of the handheld ultrasound system during the monitoring, the electronics not used for imaging.

11. The method of claim 1 wherein third scanning comprises scanning with a lesser power, smaller transmit aperture, smaller receive aperture, and smaller field of view than for the first and second scanning.

12. The method of claim 1, wherein the portable ultrasound system comprises a plurality of detectors and transmit and receive beamformers with a plurality of channels, and wherein the portable ultrasound system has filtering and compounding capability, further comprising disabling the filtering, the compounding, all but one detector of the plurality of detectors, and some of the channels of the transmit and receive beamformers in response to the detecting.

* * * * *